United States Patent
Puci et al.

(10) Patent No.: US 11,241,649 B2
(45) Date of Patent: Feb. 8, 2022

(54) TREATMENT OF OFFGAS FROM UREA FINISHING

(71) Applicant: STAMICARBON B.V., Sittard (NL)

(72) Inventors: Giusy Elisa Puci, Sittard (NL); Wilfried Marc Renaat Dirkx, Genk (BE)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 17/273,813

(22) PCT Filed: May 22, 2020

(86) PCT No.: PCT/NL2020/050326
§ 371 (c)(1),
(2) Date: Mar. 5, 2021

(87) PCT Pub. No.: WO2020/235999
PCT Pub. Date: Nov. 26, 2020

(65) Prior Publication Data
US 2021/0245089 A1 Aug. 12, 2021

(30) Foreign Application Priority Data
May 22, 2019 (EP) .................................. 19175907

(51) Int. Cl.
| B01D 47/05 | (2006.01) |
| B01D 47/06 | (2006.01) |
| B01D 47/10 | (2006.01) |
| B01D 47/12 | (2006.01) |
| B01D 53/58 | (2006.01) |

(Continued)

(52) U.S. Cl.
CPC ............. *B01D 47/06* (2013.01); *B01D 47/05* (2013.01); *B01D 47/10* (2013.01); *B01D 47/12* (2013.01); *B01D 53/58* (2013.01); *B01D 53/78* (2013.01); *B01J 2/16* (2013.01); *C07C 273/16* (2013.01);
(Continued)

(58) Field of Classification Search
CPC ........ B01D 47/06; B01D 47/05; B01D 47/10; B01D 47/12; B01D 53/58; B01D 53/78; B01D 2257/406; B01D 2258/02; B01J 2/16; C07C 273/16
See application file for complete search history.

(56) References Cited

U.S. PATENT DOCUMENTS

| 3,856,487 A | 12/1974 | Perez |
| 4,933,047 A | 6/1990 | Bannon |

FOREIGN PATENT DOCUMENTS

| EP | 2477961 B1 | 4/2016 |
| EP | 3393626 B1 | 12/2019 |

(Continued)

OTHER PUBLICATIONS

International Search Report and Written Opinion in corresponding International Patent Application No. PCT/NL2020/050326 dated Sep. 25, 2020. 10 pages.

(Continued)

*Primary Examiner* — Cabrena Holecek
(74) *Attorney, Agent, or Firm* — Leason Ellis LLP (57) ABSTRACT

Disclosed is a urea finishing method including an off-gas treatment, the method comprising urea finishing and supplying the off-gas to a quenching zone and to a scrub column comprising a sump and a venturi stage, wherein the sump has a split sump configuration with two compartments.

16 Claims, 1 Drawing Sheet

(51) Int. Cl.
*B01D 53/78* (2006.01)
*B01J 2/16* (2006.01)
*C07C 273/16* (2006.01)

(52) U.S. Cl.
CPC .... *B01D 2257/406* (2013.01); *B01D 2258/02* (2013.01)

(56) References Cited

FOREIGN PATENT DOCUMENTS

| FR | 2600553 A1 | * | 12/1987 | ............. B01D 47/06 |
|----|------------|---|---------|--------------------------|
| FR | 2600553 A1 |   | 12/1987 |                          |
| WO | 2015002535 A1 |   | 1/2015 |                          |
| WO | 2015072854 A1 |   | 5/2015 |                          |
| WO | 2017196167 A1 |   | 11/2017 |                         |

OTHER PUBLICATIONS

Wilfried Dirkx et al., "Finishing Touches", World Fertilizer, pp. 64-69. Sep. 2017. 6 pages.
Stamicarbon B.V., "The Best Available Technique for Emission Prevention in Urea Production", Stami Micromist Venturi Scrubber Leaflet. Nov. 2016. 3 pages.
Evolve Technologies Brochure, Stamicarbon B.V. 20 pages.
Evolve Technologies Brochure, Stamicarbon B.V.; Nitrogen + Syngas 2019; Mar. 4-7, 2019, Berlin. 20 pages.

* cited by examiner

FIG. 1

FIG. 2 ized particle size), for instance with particles <10 μm providing a cumulative mass of about 70 mg/Nm³. Hence, particles <10 μm account for e.g. about 50 wt. % total particulate
TREATMENT OF OFFGAS FROM UREA FINISHING

CROSS-REFERENCE TO RELATED PATENT APPLICATIONS

This application is a U.S. National Stage Application under 35 U.S.C. § 371 of International Patent Application No. PCT/NL2020/050326, filed May 22, 2020, which claims the benefit of priority of European Patent Application No. 19175907.5 filed May 22, 2019, both of which are incorporated by reference in their entireties. The International Application was published on Nov. 26, 2020, as International Publication No. WO 2020/235999 A1.

FIELD

The present invention pertains to a urea finishing method including an off-gas treatment, the method comprising solidifying urea melt and treating off-gas. The invention also pertains to a gas treatment system for treating a gas stream. The invention furthermore pertains to a urea finishing section, a urea plant, and a urea production process.

INTRODUCTION

The invention pertains to the treatment of off-gas from a urea finishing section. In a urea finishing section, a urea melt is solidified into a solid urea product using an air stream. Example types of finishing sections include prilling towers and granulation units. The finishing process typically yields an air stream containing urea dust and ammonia, referred to as off-gas. The off-gas volumes are typically very high and the off-gas is usually rather dry and hot (e.g. above 80° C. or above 100° C.). The emission limits are often stringent such as less than 20 mg/Nm³ urea dust, less than 10 mg/Nm³ or even less than 5 mg/Nm³ urea dust. The urea melt that is solidified in the finishing section comprises urea, typically at least 80 wt. % urea, and typically comprises less than 10 wt. % water, such as less than 5 wt. % water. The urea melt may comprise additional components, such as biuret and e.g. ammonium salts, for instance ammonium sulphate. The level of ammonium salts is typically less than 5 wt. % of the melt. The solid urea product typically comprises at least 90 wt. % urea, or at least 97 wt. % urea, and comprises typically further biuret and optionally other solid components, such as ammonium salts.

In urea prilling, urea melt is supplied at the top of a prilling tower, and distributed as droplets. The urea melt droplets solidify as they fall down while cooling against a large quantity of upward-moving air. Urea prills are withdrawn from the bottom. The fresh cooling air enters the bottom of the prilling tower. The off-gas comprising urea and ammonia leaves the prilling tower near the top. An example indicative air flow for a urea prilling tower is 500 000 Nm³/hr. A larger urea prilling tower may for instance have 900 000 Nm³/hr off gas with a urea capacity of 75-100 metric ton per hour.

In case the urea finishing section is a granulation unit, the granulation unit for instance has a fluidized or spouted bed. The granulation process uses for instance fluidization air and secondary air.

The off-gas from a urea prilling tower off-gas can have a peak particle size between 0.1 μm and 1 μm (as aerodynamic particle size), for instance with particles <10 μm providing a cumulative mass of about 70 mg/Nm³. Hence, particles <10 μm account for e.g. about 50 wt. % total particulate matter. Off-gas from urea granulation may for example contain about 25 mg/Nm³ of particles <10 μm. The particles are urea dust. For compliance with current and future emission limits, significant removal of submicron (<1.0 μm) particles, e.g. urea dust, is essential. Venturi scrubbers can be used for example for removing urea dust, including submicron particles, and/or for eliminating liquid entrainment.

US 2016/184758 describes a urea plant comprising a finishing section and a dust scrubbing section for treating off-gas from the finishing section. The dust scrubbing section comprises a quenching section and a venturi scrubbing section.

US 2016/303502 describes a particle capture system comprising a first quenching zone with a concentrated solution reservoir, a crossover duct, a second quench zone with a dilute solution reservoir, a venturi part, a mist eliminator and a wet electrostatic precipitator. In the first quench zone, hot gases are cooled by evaporation of aqueous quenching liquid. Dissolved particulate is collected into the water and concentrated in the reservoir of the first quench zone. Gases as they leave the quench zone and enter the scrubber vessel, are quenched again with a dilute aqueous quenching liquid. In the separation chamber, heavy droplets drop out to be collected in a dilute solution reservoir. Gases move upward through a conditioning tray (or trays), then through the multiple Venturi tubes, and move subsequently through an optional mist eliminator. Gases finally flow through the wet electrostatic precipitator to remove most remaining submicron particulate before exiting the scrubber, still according to US 20163/03502.

WO 2017/196167 describes a gas stream treatment section for urea finishing off-gas comprising a first column with an inlet, spray nozzles and a reservoir for liquid. Sprayed liquid with captured and dissolved particles is collected in the reservoir which is located under the spray nozzles. The system further comprises a horizontal venturi ejector with a nozzle, and comprises a second vertical column provided with a reservoir for recirculating urea solution used as scrubbing liquid in the nozzles of the venturi ejector.

An object of the present invention is to provide a gas treatment system and method for treating urea finishing off-gas with efficient design and stable water balance using a quenching zone and a venturi stage.

SUMMARY

Accordingly, the invention relates in a first aspect to a urea finishing method including an off-gas treatment, the method comprising:
a) supplying a urea melt and air to a finishing section, and solidifying the urea melt to give a solid urea product and off-gas, wherein the off-gas comprises urea dust and ammonia,
b) supplying the off-gas to a quenching zone and quenching the off-gas by spraying a quench liquid, to give a mixed stream comprising quench liquid and quenched off-gas, wherein the quench liquid comprises dissolved urea,
c) supplying the mixed stream comprising quench liquid and quenched off-gas to a scrub column through an inlet,
d) passing the quenched off-gas through a first mist eliminator in said scrub column and subsequently through a venturi tube comprised in a venturi stage to give a scrubbed gas stream, wherein the first mist eliminator is washed with a first wash liquid and wherein a spray liquid (lean solution) is sprayed in the gas stream in said venturi stage, wherein said scrub column comprises a sump below said first mist eliminator, wherein said sump comprises a first sump compartment and a second sump compartment which are separated from each other by a wall, wherein said inlet is arranged above said first sump compartment and wherein at least 80 wt. % of the quench liquid comprised in said mixed stream is collected in said first sump compartment, wherein the first sump compartment receives said first wash liquid from said mist eliminator;

the method further comprising:

e) recirculating liquid, which is rich sump liquid, from said first sump compartment as quench liquid to said quenching zone, and f) recirculating liquid, which is lean sump liquid, from said second sump compartment to said first mist eliminator as said first wash liquid and/or to said venturi stage as said spray liquid.

The invention pertains in a further aspect to a gas treatment system for treating a gas stream, comprising a quenching zone and a scrub column, wherein the scrub column comprises a first mist eliminator, a venturi stage and a sump, wherein the venturi stage comprises a venturi tube and a nozzle for a first spray liquid, a) wherein the quenching zone comprises an inlet for said gas stream, an inlet for quench liquid, a quench spray nozzle to spray the quench liquid into the off-gas, and an outlet for a mixed stream comprising quenched off-gas and quench liquid, b) wherein the scrub column comprises an inlet for said mixed stream connected to said outlet of said quenching zone, c) wherein the scrub column is arranged for flowing the quenched off-gas from said inlet through said first mist eliminator and subsequently through said venturi tube, d) wherein said scrub column further comprises a first nozzle for providing a wash liquid to said first mist eliminator, e) wherein said sump comprises a first sump compartment and a second sump compartment which are separated from each other by a wall, wherein the inlet for the mixed stream is arranged above said first sump compartment such that quench liquid from said mixed stream is received in said first sump compartment, f) wherein the first sump compartment is arranged for collecting wash liquid from said first mist eliminator, g) wherein the first sump compartment has an outlet for rich sump liquid connected to said inlet for quench liquid of said quenching zone, h) wherein the second sump compartment has an outlet for lean sump liquid connected to an inlet of the first nozzle of said first mist eliminator (ME1) and/or to said nozzle of said venturi stage.

DETAILED DESCRIPTION

The present invention is in part based on the judicious insight that problems in the water balance which can occur in the quenching zone due to entrapment of urea in the quenched gas stream, can be avoided by using a split sump configuration in the scrub column. The sump of the scrub column has at least two sump compartments. This allows for maintaining two different concentrations of dissolved matter (urea) in the two sump compartments to provide rich sump liquid and lean sump liquid. The rich sump liquid has a higher concentration of urea than the lean sump liquid, e.g. concentration that is at least 10 percentage point or at least 20 percentage point higher.

For instance, the rich sump liquid has a urea concentration of at least 30 wt. % or at least 40 wt. %, e.g. 40-50 wt. %, and the lean sump liquid has a urea concentration of 10 wt. % or less, or 5 wt. % or less, for instance maximum 2 wt. % urea, with the concentrations are relative to total liquid and measured in steady state operation. Preferably these concentrations are maintained by purging a part of the rich sump liquid from the first sump compartment and adding makeup water to the lean sump liquid.

The split sump configuration allows for recirculation of rich sump liquid to the quenching zone and for recirculation or supply of lean sump liquid to for example a wetted mist eliminator. The mist eliminator is arranged in the scrub column between an inlet of the scrub column, which inlet is connected to the quenching zone, and the venturi stage of the scrub column. Lean sump liquid in the lean sump compartment can overflow into the compartment for rich sump liquid. The lean sump compart is for instance closed off at the top and receives for instance liquid from at least the venturi stage and typically from at least some or even all the stages arranged above the lean sump compartment excluding a first mist eliminator.

Quench liquid containing dissolved urea is supplied with the quenched off-gas from the quenching zone to the scrub column inlet and is then collected in the first sump part wherein rich sump liquid is maintained.

The method comprises supplying a urea melt and air to a finishing section and solidifying the urea melt to give a solid urea product and off-gas. The off-gas comprises urea dust and ammonia. The air is used for cooling of the urea melt to cause solidification. The solidification step can also be referred to as a urea finishing step. The urea finishing step carried out in a finishing section, for instance a granulator, in particular a fluidized bed or spouted bed granulator, or a prilling tower. A fluidized bed granulator is preferred. Hence, the finishing involves transformation of a urea melt into a solid urea product such as prills or granules. The urea melt comprises e.g. at least 50 wt. % urea, preferably at least 90 wt. % urea and/or less than 10 wt. % water, such as less than 3 wt. % water. The urea melt optionally comprises further components, such as ammonium salts, which are included in the solid urea product. The solid product for example comprises compounds other than urea in an amount of less than 30 wt. % or less than 10 wt. % or less than 2 wt. % of the solid product, based on total compounds other than urea. The solid product comprises for instance ammonium salts in an amount of less than 20 wt. % or less than 10 wt. % total ammonium salts relative to solid product. The finishing step uses air for cooling purposes giving off-gas that comprises urea dust and ammonia. The solid urea product is for instance fertilizer grade urea.

The off-gas is supplied to an inlet of the quenching zone of the off-gas treatment system, typically through a duct. The quenching zone is for instance implemented as sprayers located in a crossover duct connecting the finishing section to the scrub column.

In the quenching zone, a quench liquid is sprayed and mixed with the off-gas, e.g. is sprayed co-current, counter current or perpendicular to the off-gas flow direction, preferably perpendicular to the off-gas flow. The quench liquid comprises water. The spraying leads to cooling by evaporation of water and to scrubbing of the gas stream such that urea dust becomes dissolved in the quench liquid. The spraying may also lead to condensation of liquid on the urea dust. In fact, typically a large part of the urea dust is scrubbed in the quenching zone, such as for example at least 30 wt. % or at least 50 wt. % of the total urea dust. The cooling by the quenching is for instance at least 10° C. or at least 30° C. The off-gas is for instance reduced in temperature from more than 80° C. to less than 50° C. The quench cooling advantageously reduces the volume of the gas stream and contributes to achieving water saturation levels of the off-gas in the off-gas treatment to provide for condensation growth of submicron urea dust particles prior to the venturi scrubbing. The quenching zone may optionally comprise a sump but preferably the quenching zone does not comprise a sump. Preferably the quenching zone is not configured for gas/liquid separation. The quenching zone has an outlet for a mixed stream comprising both the sprayed quench liquid and the quenched off-gas, this outlet is connected to an inlet of the scrub column, typically by a crossover duct. For instance in case the quenching zone is a zone with sprayers in a crossover duct between a granulator and the scrub column, the zone has an outlet for the mixed stream.

The method comprises supplying the mixed stream to an inlet of the scrub column. Preferably at least 70 wt. % or at least 90 wt. % of the sprayed quench liquid is supplied from the quenching zone to the scrub column. Preferably at least 70 vol. % or at least 90 vol. % of the quenched off-gas is supplied to the scrub column.

The method further involves passing the quenched off-gas in the scrub column through a first mist eliminator and subsequently through venturi tubes comprised in the venturi stage. Typically, the gas flows upward through the scrub column to the various stages (mist eliminators, venturi stage, and the optional acid scrub stage).

The method involves washing the first mist eliminator with a first liquid, preferably a first wash liquid, that is provided to the first mist eliminator, e.g. is sprayed to the mist eliminator. The first liquid is e.g. sprayed to the bottom or the top of the mist eliminator. The wash liquid is for instance lean sump liquid supplied from the second sump compartment.

The venturi tubes comprise, in flow direction, a converging part, a narrow part (the throat) and a diverging part. Preferably the venturi stage comprises a plurality of parallel venturi tubes, wherein the venturi tubes are for instance vertically arranged for upward flow of the gas stream. In the venturi stage, a spray liquid is sprayed in the gas stream. Preferably, the liquid is sprayed co-currently with the gas flow at the inlet of the venturi tubes and optionally liquid is also sprayed counter-currently to the gas flow at the outlet of the venturi tubes, i.e. is sprayed into the diverging part of the venturi tubes. Preferably the liquid from the venturi stage is supplied to the lean sump compartment. Preferably the spray liquid is recirculated lean sump liquid from the second sump compartment. The venturi stage provides for removal of urea dust, in particular submicron urea dust, especially in combination with a downstream mist eliminator.

The scrub column comprises a sump arranged below the first mist eliminator. In operation, the first wash liquid drains down from the mist eliminator in the direction of the sump of the scrub column.

In the invention, the sump has a split sump configuration. Accordingly, the sump comprises a first sump compartment and a second sump compartment which are separated by at least a wall comprised in the scrub column. Hence, the sump comprises a wall separating the sump compartment. More particularly, the two sump compartments are completely segregated from each other. In particular, the second sump compartment (for lean solution) also has a cover on the top part. In operation, the lean solution will overflow via an overflow in the first sump compartment for rich sump solution. The first and second sump compartments can also be referred to as a first sump and a second sump.

The wall extends in vertical direction (with respect to gravity) and provides a barrier for liquid flow between the two sump compartments. Hence, the scrub column is arranged for maintaining sump liquids with different compositions between the first and second sump compartment. In operation, the liquid level in the first compartment may also be different, preferably lower, than in the second sump compartment.

The first and the second sump compartment are each arranged below the first mist eliminator. The first sump compartment has an at least partially open top and is arranged to receive at least a part, preferably all of the liquid draining down from the first mist eliminator. The first sump compartment is preferably is arranged to receive at least a part, preferably all the first washing liquid provided to the first mist eliminator.

The second sump compartment comprises a cover plate which seals off the upper end of the second sump compartment. The second sump compartment has for instance an inlet for liquid in a sidewall, connected for instance with an outlet of the scrub column, for instance of the venturi stage. The sump comprises an overflow weir between the second and first sump compartment. The weir is e.g. provided at an upper part of the wall between the compartments. The weir allows for instance for flow from the second to the first sump compartment. This may allow for dilution of the rich sump liquid in the first sump compartment. The design with two sump compartments, one having a cover plate, is advantageously very compact. The second sump compartment provides for a buffer volume for lean sump liquid. The volume of the first sump compartment is for instance less than 100% or less than 50% or less than 40%, typically more than 10% of the volume of the second sump compartment.

The method involves recirculating a rich sump liquid from said first sump compartment as quench liquid to said quenching zone. Hence, the quench liquid sprayed in the quenching zone comprises, at least in part, said recirculating rich sump liquid. In addition the quench liquid may comprise make-up water, such as process condensate. The quench liquid may also comprise a part of the lean sump liquid withdrawn from the second sump compartment.

Preferably, the method involves supplying lean sump liquid to a duct between the finishing section (preferably granulation unit) and the quenching zone. Supplying such liquid allows for cleaning of the duct so as to remove deposits of dust (in particular urea dust from a granulator) in the duct. Such cleaning is typically necessary periodically to prevent clogging of the duct. The lean sump liquid is preferably supplied continuously to the duct to advantageously also compensate for evaporation losses of water in the quench system. The configuration of the invention advantageously allows for using lean sump liquid for such cleaning. The relatively high water concentration of the lean sump liquid advantageously allows for faster cleaning of the duct. This reduces the down time of the granulator for cleaning.

A part of the rich sump liquid is purged. This purge liquid stream is for example supplied to an evaporator where the purge liquid is heated to evaporate water from the liquid stream to give a concentrated purge stream, which has for instance a concentration of dissolved species that is at least 50% higher than before the evaporation step. The evaporator is for example a dedicated evaporator. The evaporator can also be in some embodiments, for instance, the main evaporation section of the urea plant. This main evaporation section comprises for instance a vacuum evaporation stage and receives for instance urea solution from the urea plant, usually from the recovery section of the urea plant. The evaporation section typically has an outlet for urea melt connected to an inlet of the urea finishing section. In case the purge liquid stream is supplied to the main evaporation section, typically the scrub column does not include an acid scrub stage.

The fraction of rich sump liquid that is purged in this preferred embodiment, is preferably adjusted to provide the desired urea concentration of the rich sump liquid. The part of the rich sump liquid that is not purged, is preferably recirculated.

In an embodiment with a dedicated evaporator, the evaporator is separate from the main evaporation section and has for instance a first outlet for vapor and a second outlet for the concentrated purge stream. The second outlet is hence for urea-containing liquid. This second outlet is for instance connected with a urea melt transport line that is in turn connected to the inlet for urea melt of the finishing section. In this way the concentrated purge stream is incorporated in the urea melt that is solidified in the finishing section. The concentrated purge stream from the evaporator is a liquid stream and may comprise water (e.g. in an amount of less than 30 wt. % of the total liquid stream) and dissolved species, the dissolved species include urea and can further include e.g. ammonium salts (in particular in case the acid scrub stage is used). The amount of dissolved species is usually less than 1.0 wt. % relative to the total urea melt received by the finishing section (on a time basis, e.g. per minute).

The first outlet for vapour of the dedicated evaporator is for instance connected with a condenser. The condenser has an outlet for condensate which is for instance connected to the lean sump compartment or to the rich sump compartment.

The scrub column preferably comprises an acid scrub section which is arranged above the venturi stage, with preferably a chimney tray between the acid scrub stage and the venturi stage. The acid scrub stage comprises for instance an inlet for acid scrub solution, a nozzle for spraying acid scrub solution, trays for promoting the scrubbing, and an outlet for acid solution. The acid scrub is used for removing $NH_3$ from the gas stream. The acid scrub solution comprises for instance nitric acid or sulphuric acid. The acid scrub solution from the outlet is typically in part purged as a pure stream and in part recycled. Furthermore typically make-up acid is supplied to the acid scrub inlet. The acid purge stream comprises the ammonium salt of the acid and is supplied e.g. to battery limit, or is e.g. mixed with rich sump solution from the first sump compartment. A further option is e.g. adding the acid purge, optionally after water evaporation, to the urea melt supplied to the finishing section.

The invention also pertains to a gas treatment system, or gas treatment apparatus, comprising the quenching zone and the scrub column comprising the first mist eliminator, venturi stage and sump having two sump compartments as discussed in connection with the method.

The invention also pertains to a urea finishing plant comprising a urea finishing section and a gas treatment system according to the invention. The urea finishing section comprises an inlet for urea melt, an inlet for air, an outlet for solid urea and an outlet for off-gas. The outlet for off-gas of the finishing section is connected, e.g. with a duct, to the inlet for off-gas of the quenching zone. The urea finishing unit is configured for solidifying the urea melt using air. The urea finishing section is for instance a fluidized and/or spouted bed granulator, for example a fluidized bed granulator, for instance with horizontal transport direction of granules in the fluid bed through at least two granulation compartments of the granulator and with nozzles for providing urea melt into the fluid bed in each granulation compartment. The urea finishing section can also be for instance a prilling tower.

The invention further pertains to a urea plant comprising the urea finishing plant according to the invention. The urea plant further comprises a urea melt plant. The urea melt plant comprises a high pressure synthesis section. Herein, high pressure means more than 100 bar, typically 140-180 bar. The urea melt plant further comprises a recovery section and an evaporation section. The synthesis section comprises a reactor, and preferably also a stripper and a carbamate condenser. The reactor and condenser are optionally combined in a single vessel, such as a pool reactor. The reactor has an outlet for urea synthesis solution (which comprises urea, water, ammonium carbamate and free ammonia) connected to an inlet of the stripper or an inlet of the recovery section. The stripper is a high pressure stripper and has an outlet for stripped urea solution connected to the recovery section or in some cases to the evaporation section. The stripper has an outlet for gas connected to an inlet of the condenser. The condenser has an outlet for liquid connected with an inlet of the reactor. The urea synthesis is based on the reaction of ammonia feed and $CO_2$ feed under urea forming conditions.

The stripper is for instance a vertical shell-and-tube heat exchanger configured as falling film heat exchanger with in operation a falling film of urea solution in the tubes and upward flow of gas in the tubes, and with typically a downward flow of heating fluid (such a steam) in the shell side. The stripper is for instance configured for $CO_2$ stripping, ammonia stripping, or self-stripping. The plant further comprises a $CO_2$ compressor connected for instance to the stripper in case of $CO_2$ stripping.

The carbamate condenser is for instance a shell-and-tube heat exchanger, for instance with a U-shaped tube bundle. Optionally the carbamate condenser is configured for receiving gas from the stripper in the shell side and cooling fluid in the tubes, wherein the tubes are for instance a horizontally arranged tube bundle, for instance a U-shaped tube bundle. The condenser comprises a gas distributer in the shell space for distributing the gas from the stripper.

In some embodiments the high pressure stripper and condenser are not used.

The recovery section comprises for instance a decomposer and a condenser, or for instance two decomposers in series each with a condenser. The decomposer comprises for instance an inlet for urea solution, an outlet for purified urea solution, and an outlet for gas. The decomposer is for instance configured for heating the urea solution to at least dissociate ammonium carbamate. The decomposer operates at a pressure below 100 bar. The recovery section comprises for instance a low pressure decomposer (e.g. in combination with high pressure $CO_2$ stripping), or for instance a medium pressure decomposer and a low pressure decomposer in series. The purified urea solution is supplied to an inlet of the evaporation section. The gas from the decomposer is condensed in the condenser into carbamate solution which is recycled to the synthesis section. In the evaporation section, water is evaporated from the urea solution to give a urea melt with e.g. at least 80 wt. % or at least 90 wt. % urea, and vapour, for instance using one or more vacuum evaporators. The vapour is condensed to give condensate. The condensate is typically treated in a wastewater treatment (WWT) section. The WWT section purifies the condensate and comprises for instance a desorber and a hydrolyser. The WWT comprises at least an outlet for purified process condensate.

The invention also pertains to a urea production process carried out in the inventive urea plant, comprising preparing a urea melt in the urea melt plant as described and solidifying the urea melt using air in a urea finishing section to give solid urea product and off-gas, and treating the off-gas according to the inventive method and/or in the inventive gas treatment system. The preparation of the urea melt involves reacting ammonia and $CO_2$ under urea-forming conditions in the synthesis section as described.

As used herein, for process streams (in particular urea solution), high pressure (HP) is at least 100 bara, e.g. 110-160 bara, medium pressure (MP) is 20-60 bara, low pressure (LP) is 4-10 bara. These pressure ranges are for process solutions and not necessarily the same for heating fluids such as steam. The abbreviation "bara" means bar absolute.

Preferred features of the quenching zone and scrub column mentioned in connection with the urea finishing method are also preferred for the inventive gas treatment system. The urea finishing method preferably is carried out in the gas treatment system according to the invention, preferably in a gas treatment system having the preferred features of the inventive gas treatment system.

Figure 1:
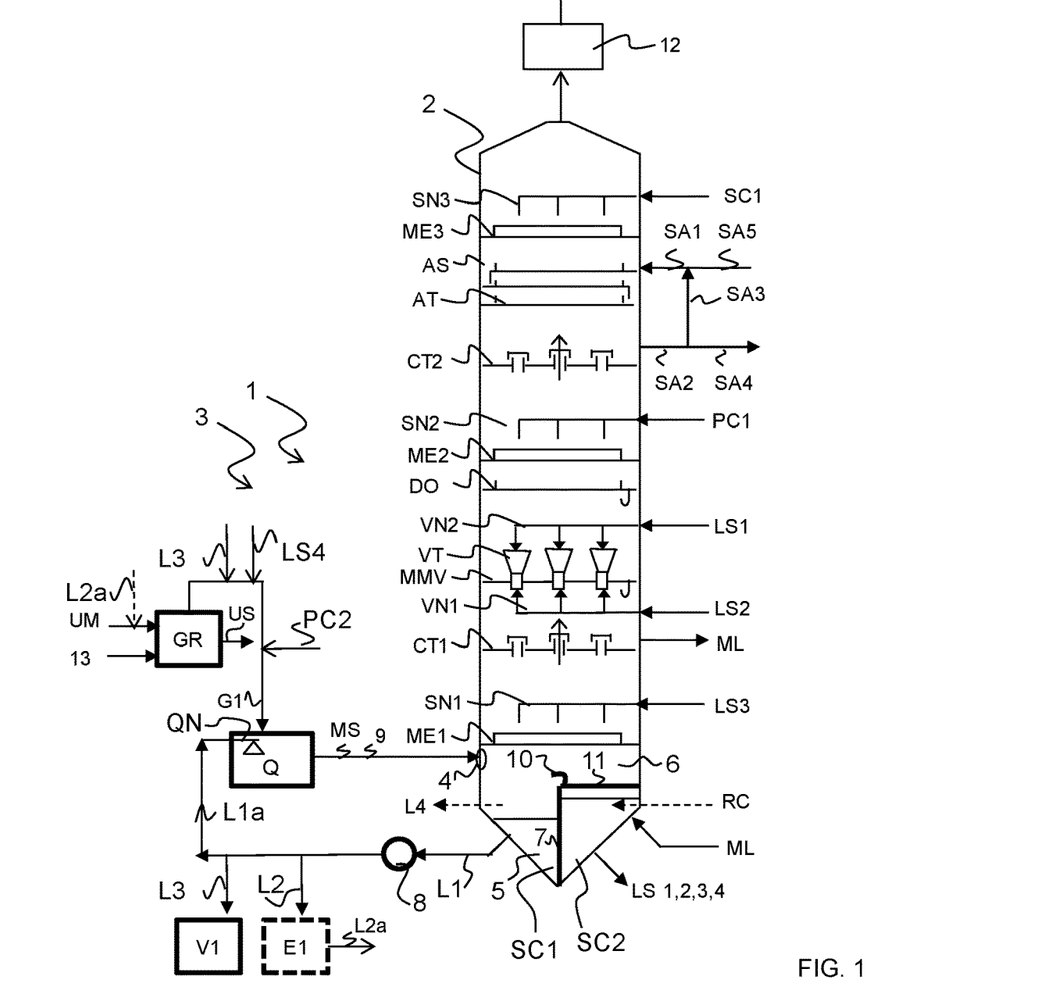
FIG. 1 schematically illustrates an example gas treatment system according to the invention.

FIG. 1 shows an example embodiment of a gas treatment system (1) according to the invention. The gas treatment system comprises a quenching zone (Q) and a scrub column (2). The gas treatment system is comprises in a urea finishing plant (3) further comprising a urea finishing section, for instance a granulator (GR). A prilling tower can also be used. The finishing section comprises an inlet for urea melt (UM) and an inlet for air (13), and comprises an outlet for solid urea (US) and an outlet for off-gas (G1). The air is for instance used as fluidization air or secondary air in the granulator or as prilling air in the prilling tower. The off-gas contains air as well as urea dust and ammonia gas. The off-gas is supplied through the quenching zone (Q). Optionally, the urea finishing plant further comprises a product cooler from which off-gas is also supplied to the quenching zone. Optionally, the urea finishing plant further comprises a classifier for size classifying the solid urea (US), e.g. using sieves, and a cooler for at least one of the fractions, such as coarse fraction, and a connection for off-gas from said cooler to the quenching zone (Q). Air from a de-dusting fan comprised in the urea finishing plant can also be supplied to the quenching zone.

In the quenching zone, a quench liquid comprising water is sprayed using a quench spray nozzle (QN) into the gas stream for cooling, including evaporative cooling, and scrubbing for urea dust removal. The quench liquid is for example sprayed perpendicular to the gas flow direction. The quenched gas and at least part or all of the quench liquid are supplied from the quenching zone (Q) as mixed stream (MF) from an outlet of the quenching zone through a flow connection, such as the duct (9), to an inlet (4) arranged at a lower part of the scrub column (2). The scrub column (2) comprises, from bottom to top, a sump (5), an inlet zone (6) at the height of the inlet (4), a first mist eliminator (ME1), a first chimney tray (CT1) and a venturi stage (MMV), for instance a venturi stage of the MultiMistVenturi type.

The venturi stage (MMV) is configured for scrubbing the gas stream and comprises a plurality of parallel venturi tubes (VT), which are each vertically arranged. Each venturi tube (VT) comprises a converging part, a throat (narrowest part) and a diverging part (in the flow direction). Each venturi tube has at the inlet side an inlet spray nozzle (VN1) and preferably each tube has a throat spray nozzle (VN2) in the outlet part (diverging part) of the tubes. In the venturi stage, small droplets and particles such as urea dust impinge on larger droplets in particular from the inlet spray nozzles (VN1) and are captured by the larger droplets. The droplets from the throat spray nozzle (VN2) contribute to particle capture as well. Hence, the venturi stage is configured for spraying a spray liquid in the gas stream through a nozzle.

Typically a droplet eliminator such as a second mist eliminator (ME2) is provided downstream of the venturi scrub stage to remove the large droplets, now containing (dissolved) urea dust particles from the gas stream. The first chimney tray (CT1) allows gas to flow up through openings in it but prevents liquid from falling down through it and for example has chimney hats. An example chimney tray is described in U.S. Pat. No. 4,933,047.

The mist eliminators as used herein are for instance independently chevron-type mist eliminators, vane type, or mesh type mist eliminators, preferably chevron-type mist eliminators. This applies for the first, second and third mist eliminator.

In some embodiments, an impingement tray (DO) is provided between the venturi tubes and the second mist eliminator. The tray is for instance a dual orifice tray. The tray is for instance flooded with liquid from the mist eliminator. The tray provides for reducing the particulate loading in the gas streams. In some embodiments, the tray (DO) and the optional holding tray for venturi tubes of the venturi stage (MMV) are optionally provided with a downcomer for instance provided as J-shaped downward tube.

Optionally, the gas treatment system (1), e.g. the scrub column (2) further comprises an acid scrub stage (AS) downstream of the venturi stage (MMV). The acid scrub serves to remove ammonia gas from the gas stream by scrubbing with acidic solution. The acid scrub stages comprises trays (AT) to which acidic liquid (SA1) is provided through an inlet. In operation, the acid (such as sulphuric acid or nitric acid) reacts with ammonia in the gas to form an ammonium salt (such as ammonium sulphate or ammonium nitrate).

In case of an acid scrub stage (AS), a second mist eliminator (ME2) is provided downstream of the venturi stage, typically with second nozzles (SN2) for providing liquid to the mist eliminator. The nozzles (SN2) are for instance arranged above or below the mist eliminator and are for example spray nozzles. The liquid is for instance make-up water, for instance provided as process condensate (PC1), typically condensate from a wastewater treatment section of a urea plant. The second mist eliminator (ME2) advantageously provides for avoiding urea entrapment in the gas stream from the venturi stage (MMV), and in particular for avoiding urea dust entrapment in the gas stream to the acid scrub stage (AS).

In case the acid scrub (AS) is arranged above the venturi stage in the scrub column (2), a second chimney tray (CT2) is provided downstream of the second mist eliminator and upstream and below the acid scrub. Acidic liquid collecting at the bottom of the acid scrub stage (AS), such as above the second chimney tray (CT2) is withdrawn through an outlet (SA2). The withdrawn acid stream is for a first part (SA3) recycled to the acid inlet (SA1) (e.g. through an acid vessel) together with make-up acid (SA5). The withdrawn acid stream (SA2) is for a second part (SA4) purged. The acid purge stream (SA4) comprises unreacted acid, the ammonium salt and possibly some urea, and is e.g. supplied to battery limit, or is e.g. mixed with rich sump liquid (L1). The acid purge stream (SA4) is for example concentrated, for instance by adding ammonium salt and possibly urea and can then be solidified, such as in case of sulphuric acid scrub to give ammonium sulfate solid fertilizer or urea ammonium sulphate solid fertilizer e.g. with at least 10 wt. % S or at least 20 wt. % S. The solidification can be done e.g. using a pelletizer, for instance with a cooling belt. The pelletizer is for instance a pelletizer as described in EP2477961. If for example nitric acid is used for the acid scrub, the resulting urea ammonium nitrate (UAN) solution can be used as liquid fertilizer, for instance by adding urea and/or ammonium nitrate up to the desired levels for agronomic use. The UAN solution obtained as product contain for example 28 wt. % to 32 wt. % of total nitrogen and typically of from 29 wt. % to 38 wt. % urea and of from 36 wt. % to 48 wt. % of ammonium nitrate, with the remainder being water. A background reference for this embodiment is EP 3393626.

In an example embodiment, the acid purge stream (SA4) is for instance mixed with rich sump solution (L1,L1a). The system comprises for instance a tank for receiving for acid stream (SA2) with an outlet for acid stream (SA2) arranged at a level higher than the overflow weir (10).

Preferably a third mist eliminator (ME3) is arranged downstream of the acid scrub (AS); this mist eliminator typically has nozzles (SN3) arranged for supplying liquid to the mist eliminator. The liquid for these nozzles (SN3) is preferably a water stream with high purity, such as steam condensate (SC1). Steam condensate is obtained e.g. by condensation of steam used as heating fluid in the urea plant.

Further optionally, a further filtration device to remove particles, such as a wet electrostatic precipitator (WESP) (not shown) is provided downstream of the acid scrub, e.g. above the third mist eliminator (ME3) in the scrub column (2), or downstream of the venturi stage (e.g. above the second mist eliminator (ME2) if the acid scrub is omitted).

The gases are withdrawn from the top of the scrub column for example using a fan (12) arranged on top of the scrub column.

The sump (5) comprises a first sump compartment (SC1) and a second sump compartment (SC2) which are separated from each other by a wall (7). In operation, the liquid level in both compartments is maintained below the upper end of the wall. The wall (7) allows for maintaining the different liquid level in the first and second compartment in operation.

Hence, in normal operation no liquid flows directly over the upper end of the wall (7) from one compartment to the other compartment. The wall (7) allows for different liquid levels to be maintained in the first and second sump compartment, with in normal operation a higher liquid level in the second sump compartment for lean sump solution than in the first compartment for rich sump solution, as shown in FIG. 1. The sump further comprises an overflow weir (10) arranged in an upper part of wall (7), which weir allows liquid to flow over the wall in a controlled way. In operation, lean sump liquid flows over the weir into the first sump compartment.

The second sump compartment (SC2) is provided with a top cover plate (11) which seals off the upper side of the compartment. Hence, liquid from the first mist eliminator (ME1) and liquid from the inlet (4) are not received in the second sump compartment and do not mix with the lean sump solution in said compartment.

The scrub column (2) further comprises first nozzles (SN1) arranged for providing liquid to the first mist eliminator (ME1), e.g. to the bottom side and/or upper side of the mist eliminator. This liquid can be used for washing of the mist eliminator.

The first mist eliminator (ME1) advantageously avoids any liquid urea entrainment in the gas stream to the venturi section (MMV) even with all the quench liquid containing dissolved urea entering the inlet zone (6).

Each of the first and the second sump compartment is arranged below the first mist eliminator (ME1), which is wetted by liquid sprayed on top of it, and is configured for receiving liquid from the first mist eliminator (ME1). The first and second sump compartments are arranged side by side and the separating wall (7) is a vertical wall between them. The first sump compartment (SC1) is located closer to the inlet (4) than the second sump compartment (SC2), i.e. the distance between the inlet (4) and the first sump compartment is smaller than the distance between the inlet (4) and the second sump compartment (SC2). For instance, in horizontal cross-section of the scrub-column (2), the first and the second scrub compartment define two opposed sides, and the inlet (4) or inlets (4) are arranged at the side of the first scrub compartment (4). The first scrub compartment is arranged below the inlet (4) and is configured for receiving liquid from the inlet (4) and for receiving at least part and preferably all of the liquid from mist eliminator (ME1).

In operation, a major part of the urea dust in the off-gas (G1) is taken up by the quench liquid in the quenching zone (Q). This liquid flows through the duct (MF) into the scrub column (2) through opening (4) and is collected in the first sump compartment (SC1), from which the rich sump liquid (L1) is taken through an outlet opening. The liquid (L1) is for a first part (L1a) recycled to the quenching zone (Q) using a pump (8), in particular to the quench spray nozzles (QN) of the quench. A second part (L2) is purged and optionally a third part (L3) of the rich sump liquid is supplied to the quench (Q) or the duct for off-gas (G1) through a mixing vessel (V1). In addition make-up water such as process condensate (PC2) is supplied to the quench (Q) or the duct for off-gas (G1).

The rich sump liquid (L1) has, for example, a urea concentration of at least 20 wt. %, preferably in the range 30-45 wt. %. This urea concentration can be controlled by adjusting the amount (L2) that is purged.

The liquid supplied to the nozzles (SN1) of the first mist eliminator (ME1) and the liquid(s) sprayed by the nozzles of the venturi stage (MMV), namely the inlet nozzles (VN1) and the optional throat nozzles (VN2), all have a much lower urea content than rich sump liquid (L1), such as a urea concentration of less than 10 wt. %, preferably less than 5 wt. %. The same applies for the liquid supplied to the second nozzles (SN2) of the second mist eliminator (ME2). The lower urea concentration and higher water mass fraction allow for further water evaporation and saturation of the gas stream in view of Raoult's law. The low urea concentration of these sprayed liquids is also important for avoiding contamination of the gas stream.

In view of the water evaporation in the quenching zone (Q) in the scrub column (2) and further in view of water loss via the purge (rich sump liquid purge (L2)) and optionally in a blow-down, make-up water (usually provided as so-called process condensate (PC1)) is supplied to the gas treatment system, in particular to at least one of the nozzles SN1, VN1, VN2, and SN2, for example to nozzle (SN2). In a preferred embodiment, make-up water is supplied, e.g. as steam condensate and/or as process condensate to the lean sump liquid compartment, for instance as liquid to the venturi stage or to a spray nozzle arranged above the venturi stage. The amount of make-up water is preferably adjusted to control the urea concentration of the lean sump liquid.

The remaining liquid for these nozzles is provided for instance by recycle of the lean sump solution (LS1, LS2, LS3) from the second sump compartment (SC2).

Liquid from the venturi stage is supplied to second sump compartment (SC2). The scrub column comprises an outlet, connection and inlet for supplying liquid from the venturi stage to the second scrub column. For example, liquid (ML) from the first chimney tray (CT1), is supplied to second sump compartment (SC2) through an appropriate outlet, flow connection, and inlet. The first chimney tray (CT1) is for example arranged to collect both liquid from the venturi stage and from the second mist eliminator. The first chimney tray (CT1) preferably prevents flow of these liquids into the first sump compartment (SC1).

The liquid in the second sump compartment (SC2) hence does not become concentrated by receiving urea contained in the liquid in the flow (MF) from the quenching zone (Q). Because some remaining urea dust is captured by the liquid flowing through first mist eliminator (MED, the liquid in the venturi stage (MMV) and the second mist eliminator (ME2), the urea concentration would increase if there is no purge. At least a part, preferably all, of the liquid supplied to the nozzles (SN1) of the first mist eliminator (MED is received by the first sump compartment (SC1) thereby effecting a purge of the lean sump liquid. Furthermore a part (LS4) of the lean sump liquid is supplied to the quenching zone (Q) and/or the duct for off-gas (G1) upstream of the quench thereby effectively providing for purge of the lean sump liquid. Make-up water for the lean sump is for instance provided to the venturi stage or to a second mist eliminator.

It was found that even in case the quenching zone has its own sump for quench liquid, urea transport through duct (9) due to urea entrapment in the quenched off-gas is very difficult to avoid leading to significant amounts of urea dust transported into the scrub column. Duct (9) is for instance a crossover duct from the finishing section (GR) to the inlet (4) comprising a quenching zone (Q).

In the invention, the rich sump liquid purge (L2) is typically subjected to an evaporation step by heating to separate water vapor from the liquid. Therefore a urea concentration of e.g. at least 20 wt. % or at least 30 wt. % in the rich sump liquid purge (L2) is advantageous for reducing energy consumption (e.g. steam consumption) required for the evaporation step. The water content of the remaining liquid (L2a) should be low (e.g. less than 0.20 wt. % or less than 0.10 wt. % or less than 0.05 wt. % relative to the urea melt) so as not disturb the operation of the finishing section, e.g. the granulator (GR). The split sump of the present invention allows for achieving this advantage of low energy consumption, in combination with a simple and compact design. Advantageously, the split sump can be as small as an undivided sump for a scrub column which reduced equipment costs.

The rich sump liquid purge (L2) is for instance supplied to an evaporator (E1), optionally through the mixing vessel (V1) and optionally with heating. The evaporator is preferably separate and distinct from the main evaporator of the urea melt plant. In the evaporator the water fraction is in part evaporated by heating. The resulting vapour is condensed in a condenser and the condensate is for instance recycled to the urea finishing plant. In an example embodiment, the vapour from the evaporator (E1) is condensed to condensate in a condenser and the condensate is optionally supplied to the second sump compartment (SC2) through an optional inlet (RC). The non-condensed vapor is e.g. supplied to the duct for off-gas (G1). The remaining liquid (L2a) in the evaporator, containing the urea removed from the off-gas (G1) is for instance mixed with urea melt (UM) to the finishing section such as the granulator (GR). In case acid purge (SA4) is mixed with rich sump liquid (L1), this introduces a small amount of ammonium salt into the urea solid product (US); however typically at a level of less than 0.5 wt. % or less than 0.20 wt. % of the solid urea such that the solid urea is still of a commercially acceptable grade, e.g. fertilizer grade. The dedicated evaporator (E1) can also be used if the rich sump liquid purge (L2) does not contain ammonium salts.

Alternatively, the purge (L2) is for instance supplied to the evaporation section of the urea plant. The evaporation section has an inlet for urea solution, an outlet for urea melt connected to the granulator, and an outlet for vapor connected to a wastewater treatment (WWT) section. For instance in case purge (L2) does not contain ammonium salts the purge is optionally supplied to the evaporation section, e. g. in case acid purge (SA4) is disposed of in a way other than by mixing with rich sump liquid (L1) (e.g. case acid purge (SA4) to battery limit) or in case the acid scrub (AS) is omitted. The WWT section is configured for purifying condensate and comprises for instance a hydrolyser for hydrolysing urea and a desorber for desorbing ammonia. Operation of a WWT section of a urea plant is usually energy intensive. Therefore a low water concentration of the purge (L2) and high urea concentration of the purge (L2) are desirable to reduce load on the main evaporator as well as on the WWT section. Optionally, some condensate from the evaporation section or purified condensate from the WWT section is supplied as make-up water to the scrub column (2), e.g. to the second sump compartment for mixing with the lean sump liquid or to the venturi stage.

The inlet zone (6) optionally comprises an outlet (L4) for overflow, e.g. to the mixing vessel (V1).

The preferred features of the various parts of the example embodiment of FIG. 1 can be used independently, and also in combination with each other. In particular, the example system and plant of FIG. 1 include as main parts the granulation unit, connecting duct, quenching zone, crossover duct, sump, mist eliminator(s), venturi stage, and acid scrub stage, and the preferred and example features of one of said parts can be used independently of the preferred and example features of the other of said parts of the system of FIG. 1.

In sum, the invention pertains in an aspect to a urea finishing method including an off-gas treatment, the method comprising urea finishing and supplying the off-gas to a quenching zone and to a scrub column comprising a sump and a venturi stage, wherein the sump has a split sump configuration with two compartments.

Figure 2:
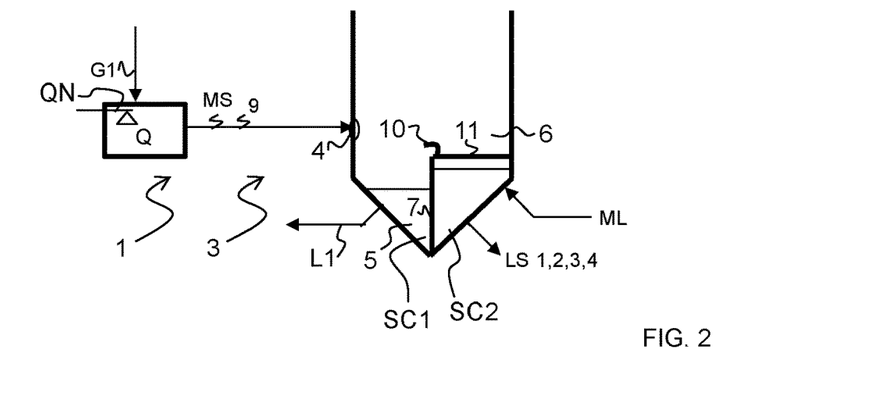
FIG. 2 schematically illustrates a quenching zone and scrub column of an example gas treatment system according to the invention.

FIG. 2 schematically illustrates a quenching zone and a bottom part of scrub column of an example gas treatment section. The reference numbers are the same as in FIG. 1.

As used herein, numeral terms like "first", "second" and "third" for items of a type do not exclude the presence of further items of the same or another type between the identified items. For instance a further chimney tray can be present between the first and the second chimney tray. The term "typically" indicates features which are advantageous but not essential. As used herein, "downstream" and "upstream" are with respect to the gas stream.

The invention claimed is:

1. A urea finishing method including an off-gas treatment, the method comprising:
   a) supplying a urea melt and air to a finishing section, and solidifying the urea melt to give a solid urea product and off-gas, wherein the off-gas comprises urea dust and ammonia,
   b) supplying the off-gas to a quenching zone and quenching the off-gas by spraying a quench liquid, to give a mixed stream comprising quench liquid and quenched off-gas, wherein the quench liquid comprises dissolved urea,
   c) supplying the mixed stream comprising quench liquid and quenched off-gas to a scrub column through an inlet,
   d) passing the quenched off-gas through a first mist eliminator in said scrub column and subsequently through a venturi tube comprised in a venturi stage to give a scrubbed gas stream, wherein the first mist eliminator is washed with a first wash liquid and wherein a spray liquid is sprayed in the gas stream in said venturi stage,
      wherein said scrub column comprises a sump below said first mist eliminator, wherein said sump comprises a first sump compartment and a second sump compartment which are separated from each other by a wall, wherein said inlet is arranged above said first sump compartment and wherein at least 80 wt. % of the quench liquid comprised in said mixed stream is collected in said first sump compartment, wherein the first sump compartment receives said first wash liquid from said first mist eliminator; the method further comprising:
   e) recirculating liquid, which is rich sump liquid, from said first sump compartment as quench liquid to said quenching zone, and
   f) recirculating liquid, which is lean sump liquid, from said second sump compartment to said first mist eliminator as said first wash liquid and to said venturi stage as said spray liquid.

2. The urea finishing method according to claim 1, further comprising:
   purging a part of the rich sump liquid from the first sump compartment, and
   adding makeup water to the lean sump liquid, wherein the lean sump liquid has a urea concentration of 5 wt. % or less and wherein the rich sump liquid has a urea concentration of at least 40 wt. %.

3. The urea finishing method according to claim 1, further comprising acid scrubbing the scrubbed gas stream using an acid scrub solution.

4. The urea finishing method according to claim 1, further comprising:
   purging a part of the rich sump liquid from the first sump compartment and heating the rich sump liquid which is purged, in an evaporator to give vapour and a concentrated purge stream; and
   combining the concentrated purge stream with the urea melt supplied to the finishing section.

5. The urea finishing method according to claim 1, wherein the finishing section is a fluid bed granulator.

6. The urea finishing method according to claim 1, further comprising supplying a part of the rich sump liquid from the first sump compartment to a duct for off-gas connecting the finishing section with the quenching zone.

7. A gas treatment system for treating a gas stream, comprising a quenching zone and a scrub column, wherein the scrub column comprises a first mist eliminator, a venturi stage and a sump, wherein the venturi stage comprises a venturi tube and a nozzle for a first spray liquid,
   a) wherein the quenching zone comprises an inlet for said gas stream, an inlet for quench liquid, a quench spray nozzle to spray the quench liquid into the gas stream, and an outlet for a mixed stream comprising quenched off-gas and quench liquid,
   b) wherein the scrub column comprises an inlet for said mixed stream connected to said outlet of said quenching zone,
   c) wherein the scrub column is arranged for flowing the quenched off-gas from said inlet through said first mist eliminator and subsequently through said venturi tube,
   d) wherein said scrub column further comprises a first nozzle for providing a wash liquid to said first mist eliminator,
   e) wherein said sump comprises a first sump compartment and a second sump compartment which are separated from each other by a wall, wherein the inlet for the mixed stream is arranged above said first sump compartment such that quench liquid from said mixed stream is received in said first sump compartment,
   f) wherein the first sump compartment is arranged for collecting wash liquid from said first mist eliminator,
   g) wherein the first sump compartment has an outlet for rich sump liquid connected to said inlet for quench liquid of said quenching zone,
   h) wherein the second sump compartment has an outlet for lean sump liquid connected to an inlet of the first nozzle of said first mist eliminator (ME1) and to said nozzle of said venturi stage.

8. The gas treatment system according to claim 7, wherein said first mist eliminator is a chevron type mist eliminator.

9. A urea finishing plant comprising the gas treatment system according to claim 7 and a urea finishing section, wherein the urea finishing section comprises an inlet for urea melt, an inlet for air, an outlet for solid urea and an outlet for off-gas which is connected to the inlet of the quenching zone and wherein the urea finishing section is configured for solidifying the urea melt using the air.

10. The urea finishing plant according to claim 9, wherein the urea finishing section is a fluidized bed granulator.

11. The urea finishing plant according to claim 9, wherein the scrub column further comprises an acid scrub section above the venturi stage.

12. The urea finishing plant according to claim 9 further comprising an evaporator having an inlet in fluid connection with said outlet for rich sump, wherein the evaporator further has an outlet for urea-containing liquid and an outlet for vapour, wherein the outlet for urea-containing liquid is connected with a urea melt transport line connected to the inlet for urea melt of said finishing section.

13. The urea finishing plant according to claim 9, wherein the sump comprises an overflow weir at an upper part of said wall and wherein said second sump compartment comprises a cover plate sealing off the upper side of the second sump compartment.

14. The urea finishing plant according to claim 9, wherein the first mist eliminator comprised in said gas treatment system is a chevron type mist eliminator.

15. The urea finishing plant according to claim 9, wherein the urea finishing section is a spouted bed granulator.

16. The urea plant comprising the urea finishing plant according to claim 9 and further comprising a urea melt plant, wherein the urea melt plant comprises a high pressure synthesis section, a recovery section and an evaporation section, wherein the high pressure synthesis section comprises a reactor, a stripper and a carbamate condenser.

* * * * *